United States Patent
Slater et al.

[11] Patent Number: 5,951,488
[45] Date of Patent: Sep. 14, 1999

[54] ENDOSCOPIC MULTIPLE SAMPLE BIOPTOME

[75] Inventors: Charles R. Slater, Fort Lauderdale; Matthew A. Palmer, Miami; Jurgen Andrew Kortenbach, Miami Springs; Michael Sean McBrayer; Saul Gottlieb, both of Miami, all of Fla.

[73] Assignee: Symbiosis Corporation, Miami, Fla.

[21] Appl. No.: 08/758,693

[22] Filed: Dec. 3, 1996

Related U.S. Application Data

[60] Continuation of application No. 08/459,479, Jun. 2, 1995, Pat. No. 5,647,125, which is a division of application No. 08/189,937, Feb. 1, 1994, Pat. No. 5,542,432, which is a continuation-in-part of application No. 07/837,046, Jan. 29, 1992, Pat. No. 5,507,296.

[51] Int. Cl.⁶ ..................................................... A61B 5/00
[52] U.S. Cl. ............................................................ 600/564
[58] Field of Search ........................... 128/749, 751–754; 606/167, 170, 205–208; 600/562, 564–567

[56] References Cited

U.S. PATENT DOCUMENTS

| | | | |
|---|---|---|---|
| 2,850,007 | 9/1958 | Lingley | 128/2 |
| 3,001,522 | 9/1961 | Silverman | 600/567 |
| 3,175,554 | 3/1965 | Stewart | 128/2 |
| 3,404,677 | 10/1968 | Springer | 600/564 |
| 3,590,808 | 7/1971 | Muller | 128/2 B |
| 3,989,033 | 11/1976 | Halpern et al. | 128/2 B |
| 3,989,049 | 11/1976 | Yoon | 606/141 |
| 4,200,111 | 4/1980 | Harris | 128/751 |
| 4,282,884 | 8/1981 | Boebel | 128/751 |
| 4,393,872 | 7/1983 | Reznik et al. | 604/151 |
| 4,522,206 | 6/1985 | Whipple et al. | 128/312 |
| 4,644,951 | 2/1987 | Bays | 128/305 |
| 4,651,752 | 3/1987 | Fuerst | 128/754 |
| 4,651,753 | 3/1987 | Lifton | 128/751 |
| 4,721,116 | 1/1988 | Schintgen et al. | 128/751 |
| 4,733,662 | 3/1988 | DeSatnick et al. | 128/305 |
| 4,763,668 | 8/1988 | Macek et al. | 128/751 |
| 4,817,630 | 4/1989 | Schintgen et al. | 128/751 |
| 4,881,550 | 11/1989 | Kothe | 128/752 |
| 4,896,678 | 1/1990 | Ogawa | 128/751 |
| 4,909,782 | 3/1990 | Semm et al. | 606/171 |
| 4,953,559 | 9/1990 | Salerno | 128/751 |
| 5,052,402 | 10/1991 | Bencini et al. | 128/751 |
| 5,082,000 | 1/1992 | Picha et al. | 128/751 |
| 5,085,658 | 2/1992 | Meyer | 606/46 |
| 5,133,727 | 7/1992 | Bales et al. | 606/170 |
| 5,171,255 | 12/1992 | Rydell | 606/170 |
| 5,172,700 | 12/1992 | Bencini et al. | 128/751 |
| 5,195,533 | 3/1993 | Chin et al. | 128/754 |
| 5,217,458 | 6/1993 | Parins | 606/48 |
| 5,217,468 | 6/1993 | Clement | 606/127 |
| 5,219,357 | 6/1993 | Honkanen et al. | 606/205 |
| 5,228,451 | 7/1993 | Bales et al. | 128/751 |
| 5,234,000 | 8/1993 | Hakky et al. | 128/751 |
| 5,238,002 | 8/1993 | Devlin et al. | 128/754 |
| 5,251,641 | 10/1993 | Xavier | 128/754 |
| 5,281,230 | 1/1994 | Heidmueller | 606/127 |
| 5,318,589 | 6/1994 | Lichtman | 606/205 |
| 5,334,198 | 8/1994 | Hart et al. | 606/52 |

Primary Examiner—Max Hindenburg
Attorney, Agent, or Firm—Finnegan, Henderson, Farabow, Garrett, & Dunner, L.L.P.

[57] ABSTRACT

An endoscopic multiple sample bioptome includes a hollow outer member and an axially displaceable inner member extending therethrough. The proximal ends of the outer and inner members are coupled to an actuator for axially displacing one relative to the other. The distal end of the outer member is coupled to one of a cylinder having a sharp distal edge and a jaw assembly, while the distal end of the inner member is coupled to the other. The jaw assembly includes a pair of opposed, preferably toothed jaw cups each of which is coupled by a resilient arm to a base member. The arms are bent to urge the jaws away from each other. The base member is mounted inside the cylinder and axial movement of the jaw assembly and cylinder relative to each other draws the arms into the cylinder and brings the jaw cups together in a biting action. When the outer member is coupled to the jaw assembly and the inner member is coupled to the cylinder, the distal end of the inner member is preferably coupled to the cylinder by a bent end which is welded to a hole in the cylinder wall. One of the jaws is preferably larger and has a pair of proximal wings. The wings and an upper edge portion of the larger jaw are bent radially inward and enter the smaller jaw when the jaws are closed.

23 Claims, 9 Drawing Sheets

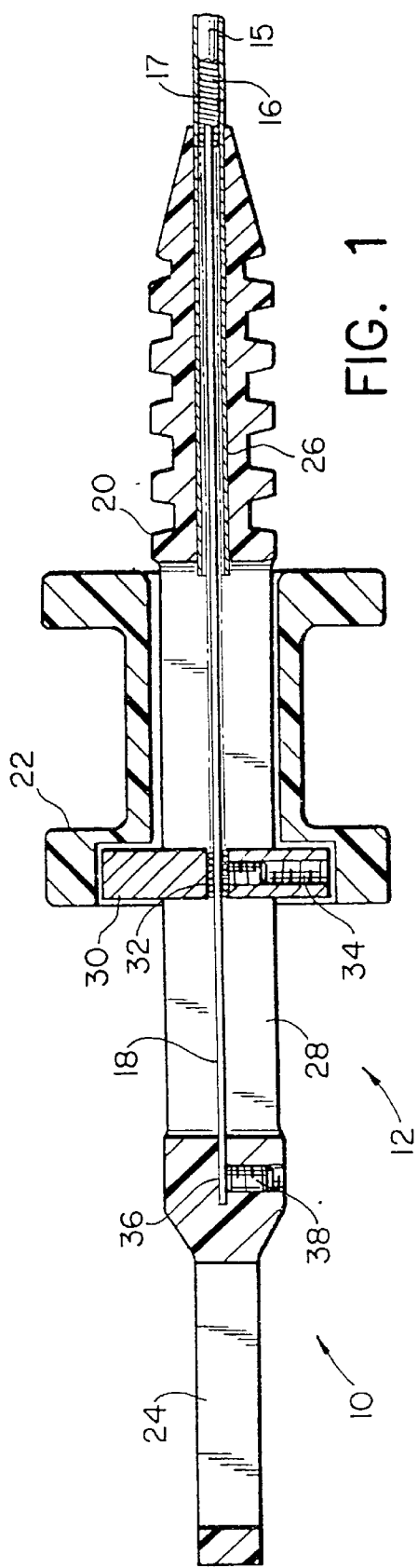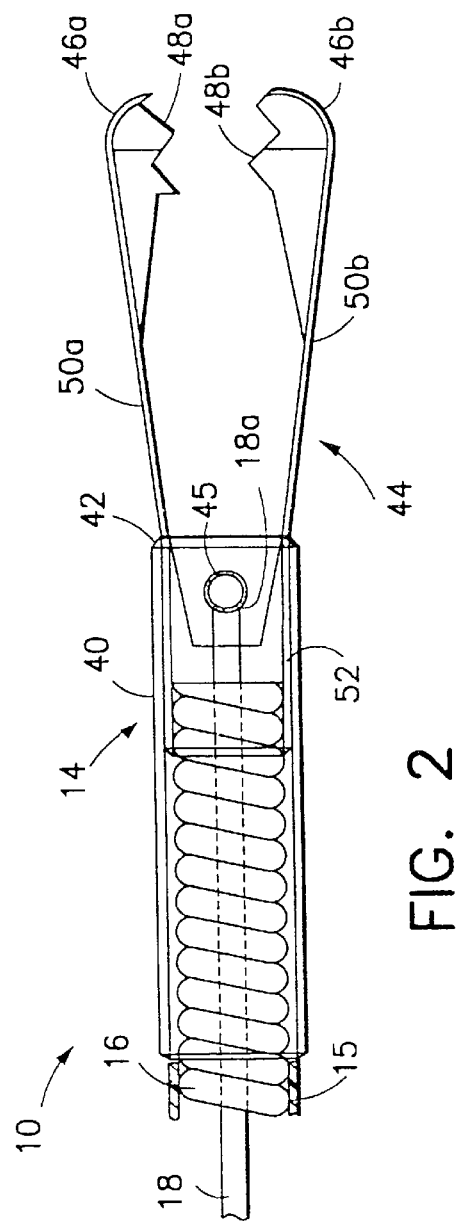

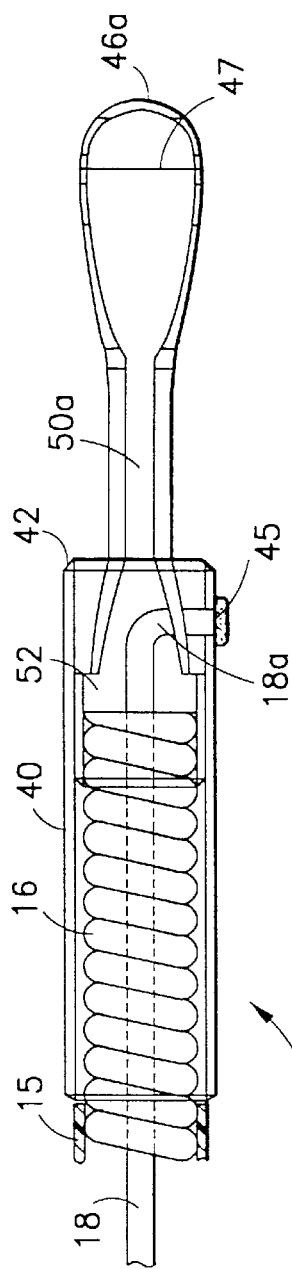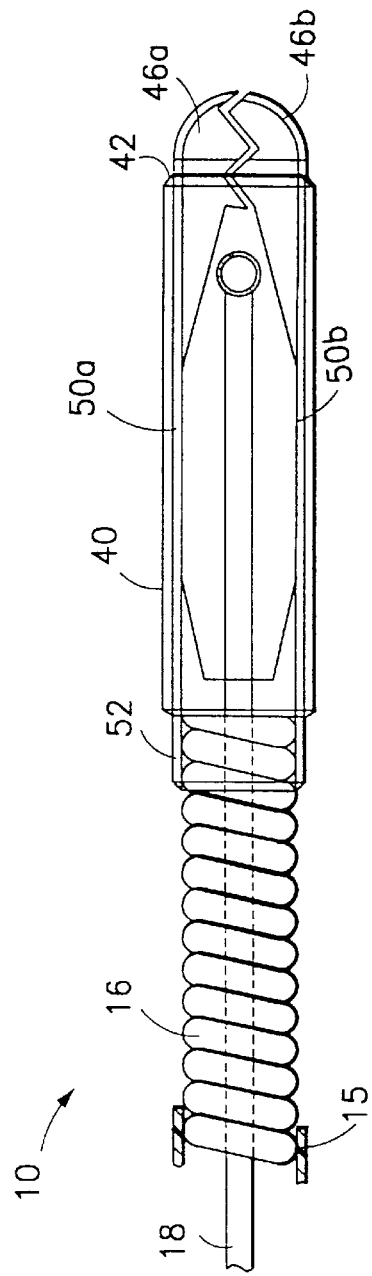

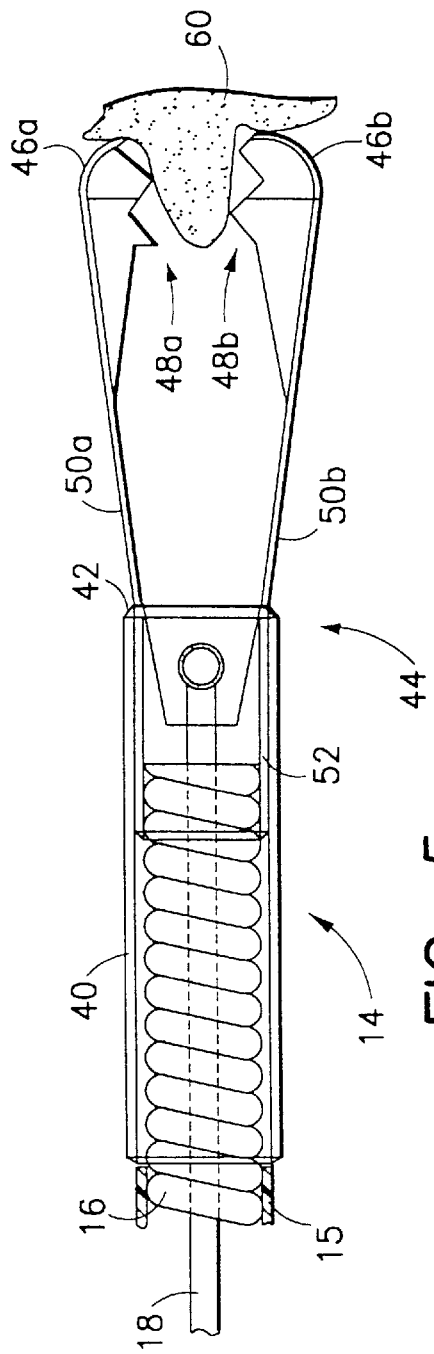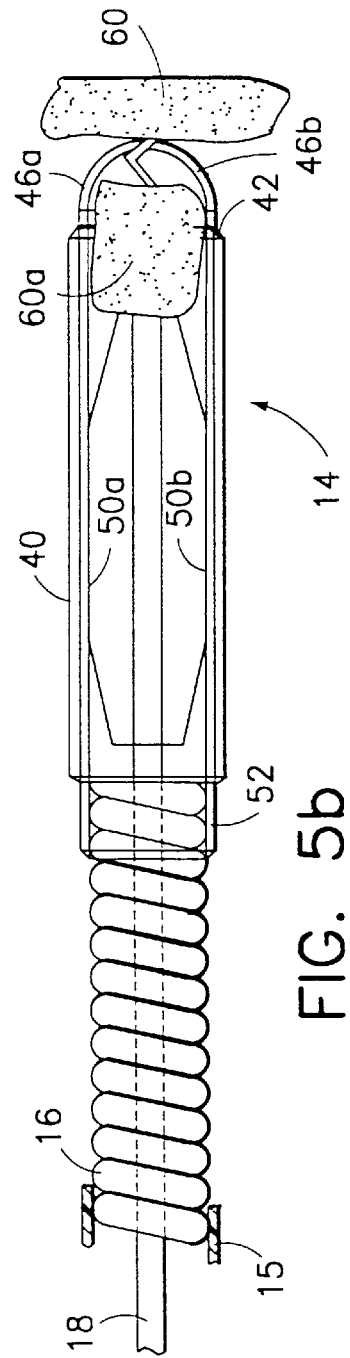
FIG. 5a
FIG. 5b

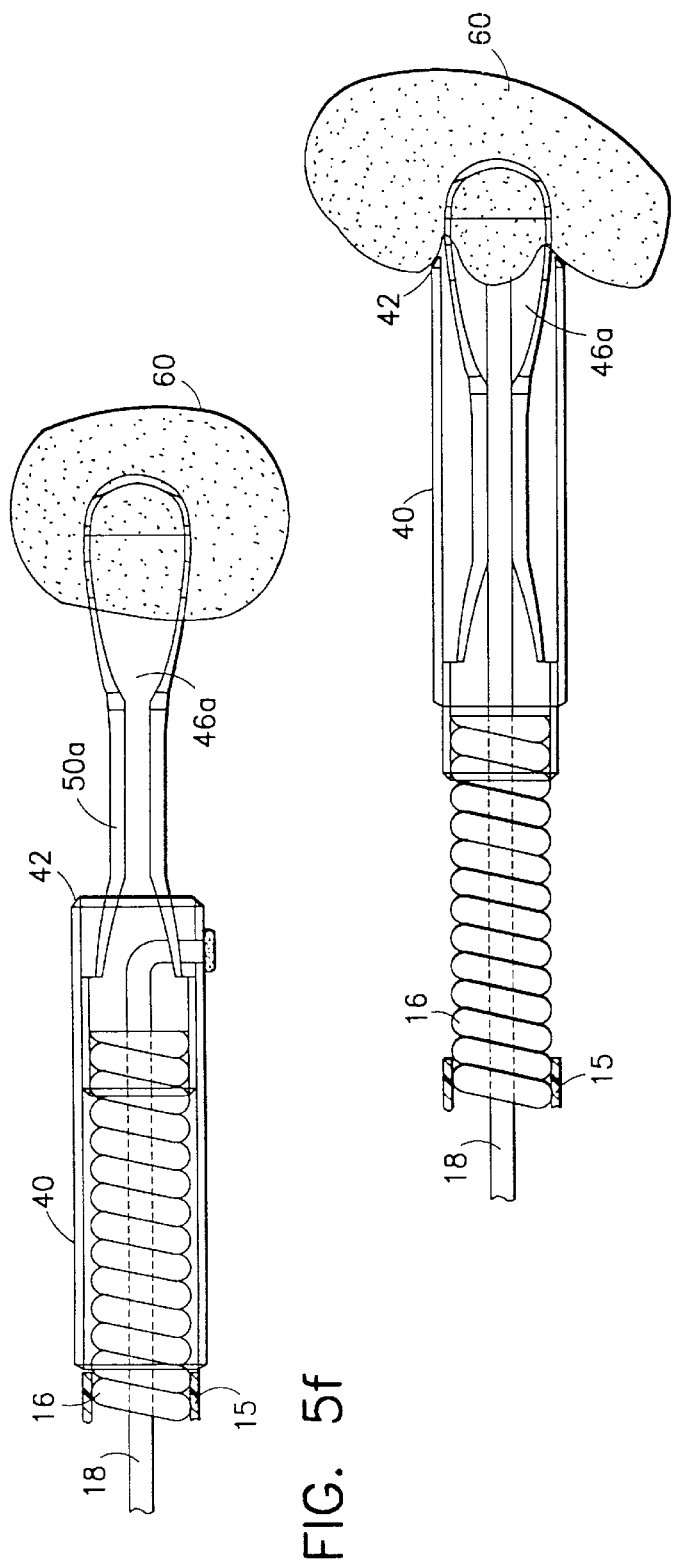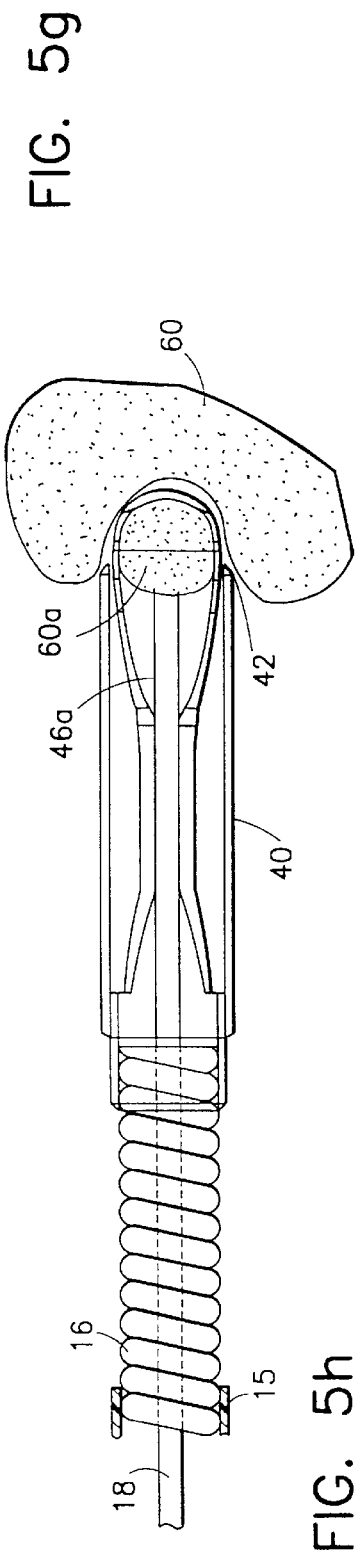

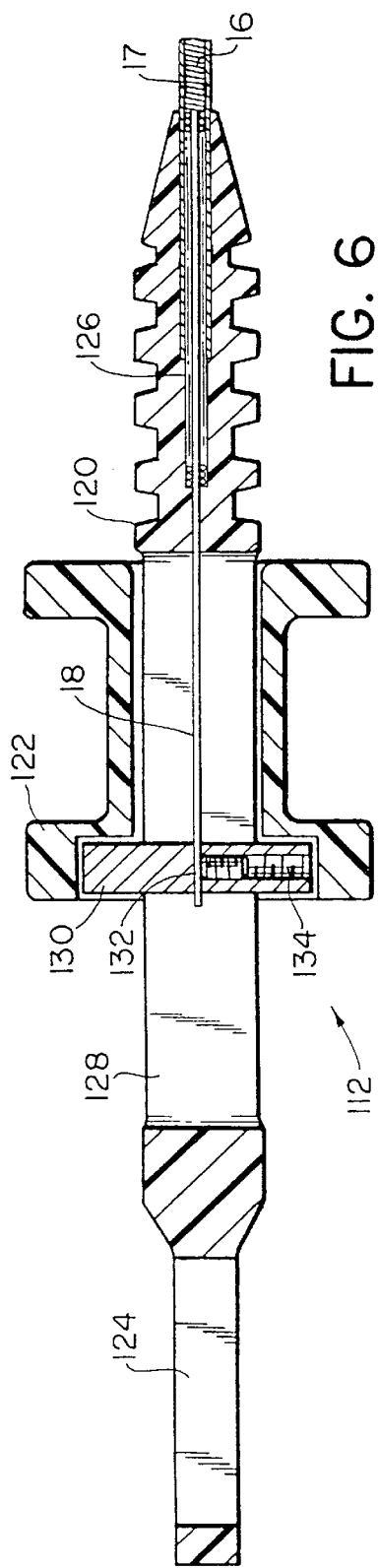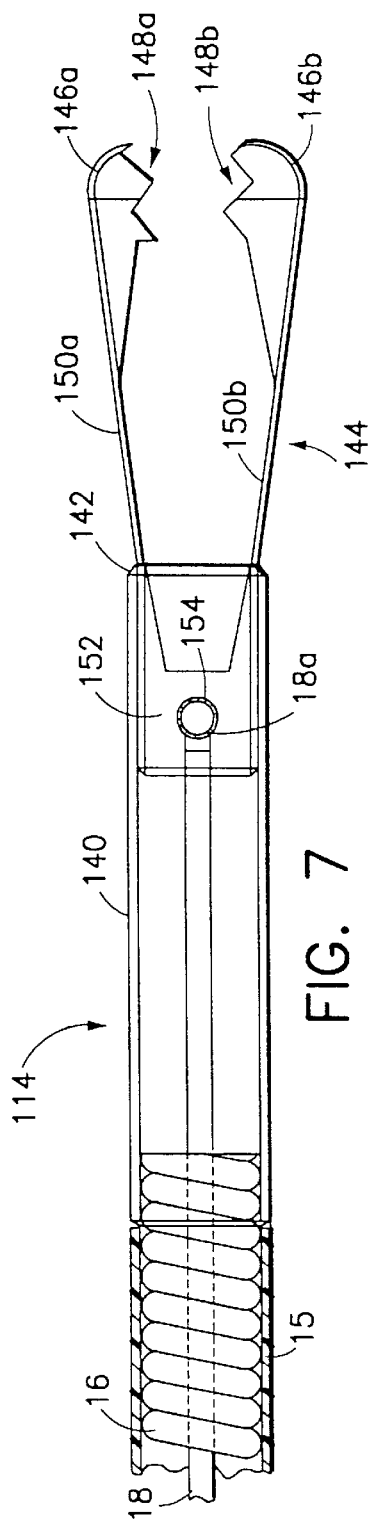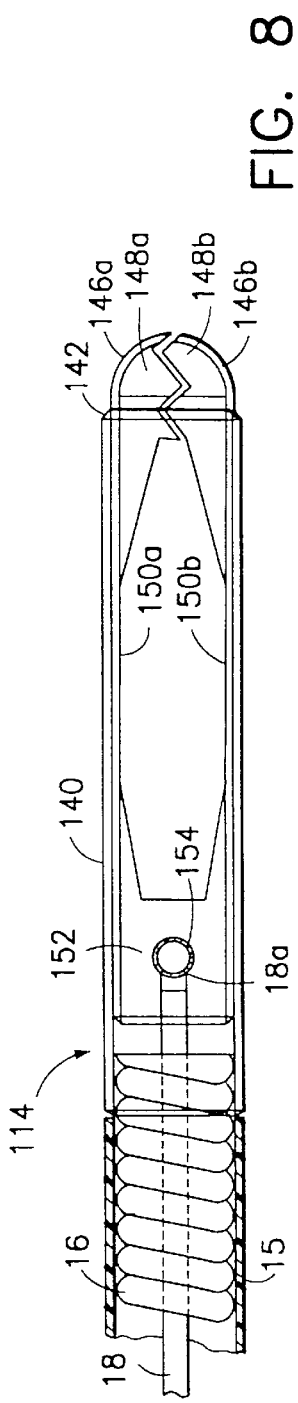

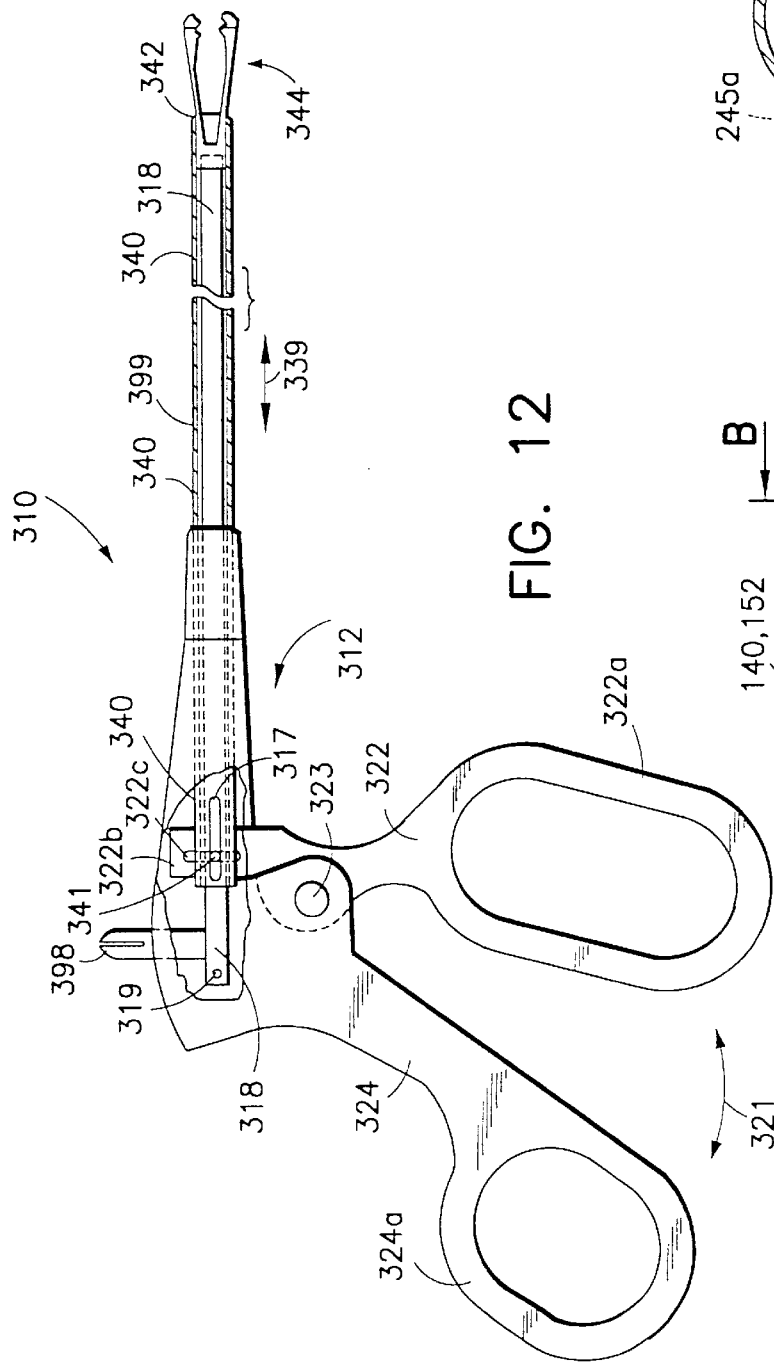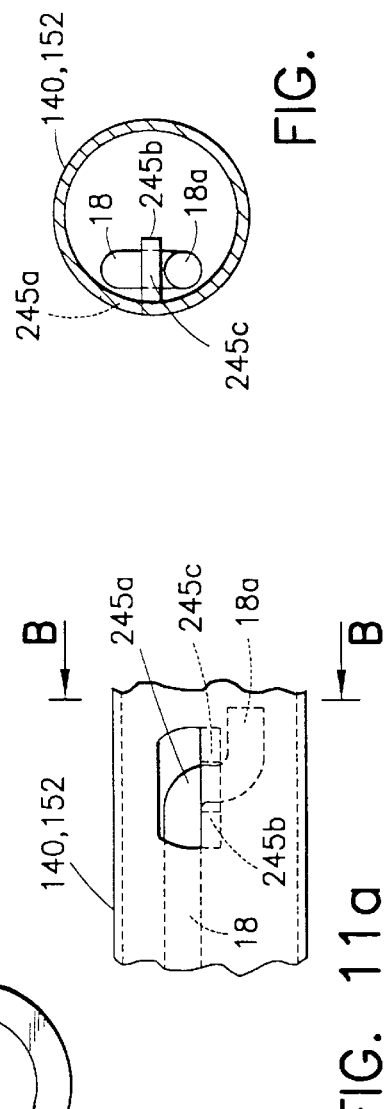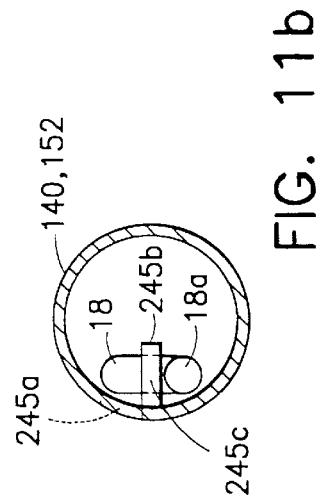

ENDOSCOPIC MULTIPLE SAMPLE BIOPTOME

This application is a continuation of application Ser. No. 08/459,479, filed on Jun. 2, 1995, now U.S. Pat. No. 5,647,115 which is a divisional of Ser. No. 08/189,937, filed on Feb. 1, 1994, and now issued as U.S. Pat. No. 5,542,432, which is a continuation-in-part of application Ser. No. 07/837,046 filed Feb. 18, 1992, now U.S. Pat. No. 5,507,296 which are hereby incorporated by reference herein in their entireties.

BACKGROUND OF THE INVENTION

1. Field of the Invention

This invention relates to endoscopic surgical instruments. More particularly, this invention relates to an instrument for taking multiple biopsy tissue samples.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. The single-sample limitation of most bioptomes is due to the limited space between the biopsy forceps jaws. Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope. Thus, several known multiple sample biopsy instruments are precluded from use with an endoscope because of their size and rigidity. These include the "punch and suction type" instruments disclosed in U.S. Pat. No. 3,989,033 to Halpern et al. and No. 4,522,206 to Whipple et al. Both of these devices have a hollow tube with a punch at the distal end and a vacuum source coupled to the proximal end. A tissue sample is cut with the punch and suctioned away from the biopsy site through the hollow tube. It is generally recognized, however, that suctioning tissue samples through a long narrow flexible bioptome is virtually impossible.

Efforts have been made to provide a multiple sampling ability to an instrument which must traverse the narrow lumen of an endoscope. These efforts have concentrated on providing a cylindrical storage space at the distal end of the instrument wherein several tissue samples can be accumulated before the instrument is withdrawn from the endoscope. U.S. Pat. No. 4,651,753 to Lifton, for example, discloses a rigid cylindrical member attached to the distal end of a first flexible tube. The cylindrical member has a lateral opening and a concentric cylindrical knife blade is slidably mounted within the cylindrical member. A second flexible tube, concentric to the first tube is coupled to the knife blade for moving the knife blade relative to the lateral opening in the cylindrical member. A third flexible tube having a plunger tip is mounted within the second flexible tube and a vacuum source (a syringe) is coupled to the proximal end of the third tube. A tissue sample is taken by bringing the lateral opening of the cylindrical member upon the biopsy site, applying vacuum with the syringe to draw tissue into the lateral opening, and pushing the second flexible tube forward to move the knife blade across the lateral opening. A tissue sample is thereby cut and trapped inside the cylindrical knife within the cylindrical member. The third flexible tube is then pushed forward moving its plunger end against the tissue sample and pushing it forward into a cylindrical storage space at the distal end of the cylindrical member. Approximately six samples can be stored in the cylindrical member, after which the instrument is withdrawn from the endoscope. A distal plug on the cylindrical member is removed and the six samples are collected by pushing the third tube so that its plunger end ejects the samples.

The device of the Lifton patent suffers from several recognizable drawbacks. First, it is often difficult to obtain a tissue sample laterally of the device. Second, in order to expedite the obtaining of a lateral sample, a syringe is used to help draw the tissue into the lateral opening. However, this causes what was once a two-step procedure (position and cut), to become a three-step procedure (position, suction, cut). In addition, the use of a syringe requires an additional hand. Third, the Lifton patent adds a fourth step to the biopsy procedure by requiring that the tissue sample be pushed into the storage space. Thus, in all, the Lifton patent requires substantial effort on the part of the surgeon and an assistant and much of this effort is involved in pushing tubes, an action which is counter-intuitive to classical biopsy sampling. The preferred mode of operation of virtually all endoscopic tools is that a gripping action at the distal end of the instrument is effected by a similar action at the proximal end of the instrument. Classical biopsy forceps jaws are closed by squeezing a manual actuation member in a syringe-like manner.

A more convenient endoscopic multiple sample biopsy device is disclosed in U.S. Pat. No. 5,171,255 to Rydell. Rydell provides a flexible endoscopic instrument with a knife-sharp cutting cylinder at its distal end. A coaxial anvil is coupled to a pull wire and is actuated in the same manner as conventional biopsy forceps. When the anvil is drawn into the cylinder, tissue located between the anvil and the cylinder is cut and pushed into a storage space within the cylinder. Several samples may be taken and held in the storage space before the device is withdrawn from the endoscope. While the device of Rydell is effective in providing a multiple sample tool where each sample is obtained with a traditional two-step procedure (position and cut), it is still limited to lateral cutting which is often problematic. Traditional biopsy forceps provide jaws which can grasp tissue frontally or laterally. Even as such, it is difficult to position the jaws about the tissue to be sampled. Lateral sampling is even more difficult.

In addition to the biopsy procedure described above, it is also sometimes necessary to obtain biopsy samples using an endoscopic tool which is inserted into a body cavity through a trocar tube or directly into a body cavity. These procedures typically involve the taking of tissue samples from the cervix. Many of the problems facing the "flexible" biopsy forceps which are used in an endoscope are not present in the gynecological biopsy procedure. Nevertheless, it is still often necessary or desirable to take multiple cervical samples and the repeated insertion and withdrawal of the bioptome prolongs the procedure and increases the trauma to the patient.

SUMMARY OF THE INVENTION

It is therefore an object of the invention to provide an endoscopic multiple sample bioptome which is not limited to lateral tissue sampling.

It is also an object of the invention to provide an endoscopic multiple sample bioptome which is easy to operate.

It is another object of the invention to provide an endoscopic multiple sample bioptome which is inexpensive to manufacture.

It is still another object of the invention to provide an endoscopic multiple sample bioptome which has all of the advantages of traditional biopsy forceps with the added ability to collect multiple samples.

In accord with these objects which will be discussed in detail below, the endoscopic multiple sample bioptome of the present invention includes a relatively long flexible member having a lumen with an axially displaceable wire extending therethrough. The proximal ends of the flexible member and wire are coupled to a manual actuation means for axially displacing one of the flexible member and wire relative to the other. The distal end of the flexible member is coupled to one of a cylinder having a knife sharp distal edge and a jaw assembly. The distal end of the wire is coupled to the other of the cylinder and the jaw assembly. The jaw assembly includes a pair of opposed toothed jaw cups each of which is coupled by a narrow arm to a base member. The narrow arm of each jaw is a resilient member which urges each jaw away from the other. The base member of the jaw assembly is mounted inside the cylinder and axial movement of one of the jaw assembly and cylinder relative to the other draws the necks of the jaws into the cylinder or moves the cylinder over the necks of the jaws to bring the jaw cups together in a biting action.

Preferred aspects of the invention include: forming the jaw assembly from a single piece of spring steel; coupling the distal end of the coil to the jaw assembly; coupling the cylinder to the axially displaceable wire; and providing the coil with a stiffening sheath or wire along substantially its entire length. It is additionally preferred that the distal end of the wire be coupled to the cylinder by welding, but other means such as a Z-bend in the distal end of the wire which enters and engages a punched and bent portion of the cylinder wall may be used.

According to another embodiment of the invention, an endoscopic multiple sample bioptome is provided with a relatively rigid hollow tube having a relatively rigid rod extending therethrough. The distal end of the rod is coupled to a jaw assembly and the distal end of the tube is provided with a knife-sharp edge. The proximal end of the rod is coupled to a fixed portion of a handle and the proximal end of the tube is coupled to a movable portion of the handle. Movement of the movable portion of the handle results in longitudinal movement of the tube relative to the rod and effects and closing of the jaws as described above. The fixed portion of the handle is preferably provided with a thumb ring and the movable portion of the handle is preferably provided with a finger ring. The handle is gripped in pistol-like manner and squeezing the movable portion towards the fixed portion effects a closing of the jaws.

According to yet another embodiment of the invention, the jaw assembly is formed from a single cylindrical piece of spring steel having a substantially hemispherical end. The cylinder is cut by wire EDM (electrical discharge machining) and/or laser machining to provide a lower jaw having a larger jaw cup than the upper jaw. The lower jaw is also provided with a pair of proximally extending wings. The jaw teeth are preferably formed so that they are as small as possible but with the proximal teeth having greater clearance than the distal teeth, e.g. by providing the proximal teeth with a sharper angle than the distal teeth.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevation view in partial section of the proximal end of a first embodiment of the invention;

FIG. 2 is an enlarged transparent side elevation view of the distal end of a first embodiment of the invention with the jaws open;

FIG. 3 is an enlarged transparent top view of the distal end of a first embodiment of the invention;

FIG. 4 is a view similar to FIG. 2, but with the jaws closed;

FIGS. 5a through 5e are views similar to FIGS. 2 and 4 showing a sequence of biopsy sampling operations;

FIGS. 5f and through 5h are views similar to FIG. 3 showing the cutting action of the knife-sharp distal edge of the cylinder;

FIG. 6 is a view similar to FIG. 1 of the proximal end of a second embodiment of the invention;

FIG. 7 is a view similar to FIG. 2 of the distal end of a second embodiment of the invention with the jaws open;

FIG. 8 is a view similar to FIG. 7, but with the jaws closed;

FIG. 10a is an enlarged broken side elevation view of a different embodiment of control wire coupling;

FIG. 10b is a cross sectional view along line B—B in FIG. 10a;

FIG. 11a is a view similar to FIG. 10a but of yet another embodiment of control wire coupling;

FIG. 11b is a cross sectional view along line B—B of FIG. 11a;

FIG. 12 is a broken side elevation view in partial section of third embodiment of the invention;

DETAILED DESCRIPTION OF THE PREFERRED EMBODIMENTS

Figure 5C:
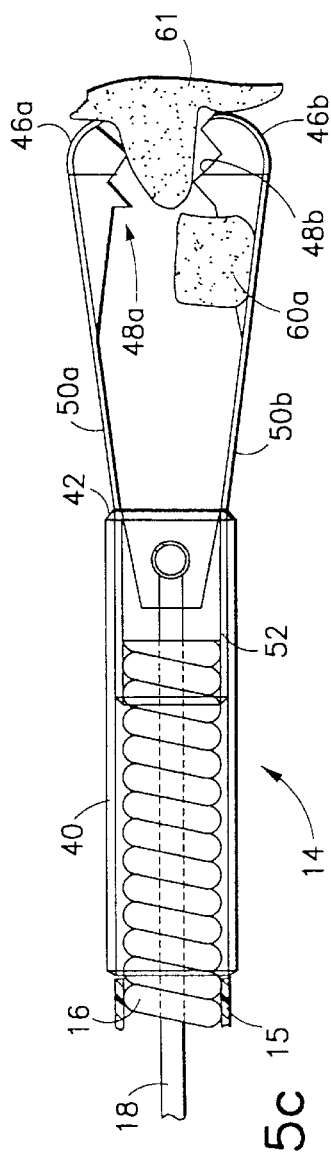

Referring now to FIGS. 1 through 4, a first embodiment of the multiple sample bioptome 10 includes a proximal handle 12 and a distal end effector 14. A long flexible coil 16 having an axially displaceable control wire 18 extending therethrough couples the handle 12 and the end effector 14. The coil 16 is preferably covered with a PTFE, FEP or polyolefin sheath 15 along substantially all of its length and a strain relief sleeve 17 covering a portion of the coil which extends from the handle 12. The control wire 18 is preferably flexible but longitudinally inelastic and is ideally formed from 304 Steel and provided with and outer diameter of approximately 0.018 inch. The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The displaceable spool 22 is provided with a cross member 30 which passes through the slot 28 in the central shaft 20. The cross member 30 is provided with a central through hole 32 and a radially engaging set screw 34. According to the first embodiment of the invention, a short bore 36 and a radially engaging set screw 38 are provided in the shaft 20 distal of the thumb ring 24 with the bore 36 communicating with the longitudinal slot 28. In the first embodiment of the invention, the proximal end of the coil 16 extends into the central through hole 32 in the cross member 30 and is fixed there by the set screw 34. The proximal end of the control wire 18, passes through slot 28, is inserted into the short bore 36, and held there by the set screw 38. From the foregoing, those skilled in the art will appreciate that relative movement of the shaft 20 and spool 22 results in movement of the control wire 18 relative to the coil 16. Such action results in actuation of the end effector 14 as described in detail below.

Turning now to FIGS. 2 through 4, the end effector 14 includes a cylindrical sleeve 40 having a knife-sharp distal edge 42, and a jaw assembly 44. The jaw assembly 44 includes a pair of opposed jaw cups 46a, 46b each preferably having a plurality of sharp teeth 48a, 48b. A resilient, preferably narrow, arm 50a, 50b extends proximally from each jaw cup 46a, 46b. A cylindrical base member 52 joins the proximal ends of the arms 50a, 50b. Because the arms 50a, 50b and the jaws 46a, 46b are preferably formed from a deep drawn piece of spring steel as discussed in more detail below, as seen best in FIG. 2, the narrow resilient arms 50a, 50b may be bent apart from each other, thereby urging the jaw cups 46a, 46b apart. According to the first embodiment of the invention, the cylindrical base member 52 is coupled to the distal end of the flexible coil 16 by welding, soldering, crimping, or any other suitable manner. The cylindrical sleeve 40 is coupled to the distal end of the control wire 18 by providing the sleeve 40 with a lateral hole which engages a bent end 18a of the control wire 18. As shown in FIGS. 2 through 4, the bent end 18a of the control wire 18 is welded to the hole 45 in the side of the sleeve 40. However, as will be described in detail herein below, other methods of coupling the control wire to the sleeve are possible. The cylindrical sleeve 40 is slidably mounted over the cylindrical base member 52 as shown in FIGS. 2 and 3 and is axially movable over the resilient arms 50a, 50b as shown in FIG. 4.

As seen in FIG. 3, the jaw cups 46a, 46b have an eccentric cross section with their widest point indicated by the line 47. Distal of the line 47, the jaw cups are substantially hemispherical and proximal of the line 47, the jaw cups are substantially hemi-elliptical. The teeth 48a, 48b are arranged so that the jaws interlock when closed as shown in FIG. 4. If the jaws are formed by wire EDM, teeth are formed only on the sides of the jaws. If the jaws are formed by laser cutting, however, it is possible to arrange the teeth radially along the sides and the front of the jaws. It will also be seen that the side walls of the jaw cups 46a, 46b taper towards the arms 50a, 50b to provide a smooth transition from the jaw cups to the arms.

From the foregoing description and with reference to FIGS. 1 through 4, those skilled in the art will appreciate that when the spool 22 and the shaft 20 are axially displaced relative to each other, the cylindrical sleeve 40 and the jaw assembly 44 are similarly axially displaced relative to each other, from the positions shown in FIG. 2 to the positions shown in FIG. 4 and vice versa. It will also be appreciated that when the spool 22 and shaft 20 are in the approximate position shown in FIG. 1, the cylindrical sleeve 40 and the jaw assembly 44 will be in the approximate position shown in FIG. 2; i.e., with the jaws open. Thus, those skilled in the art will further appreciate that when the spool 22 is moved towards the thumb ring 24, or vice versa, the cylindrical sleeve 40 and the jaw assembly 44 will be brought into the approximate position shown in FIG. 4; i.e., with the jaws closed. Moreover, it will also be appreciated that it is preferable to move the thumb ring 24 relative to the spool 22, rather than vice versa since that will move the cylindrical sleeve 40 relative to the jaw assembly 44 rather than vice versa. This is desirable so that the jaw assembly is not moved away from a tissue sample while the jaws are being closed.

Turning now to FIGS. 5a through 5e, the operation of the multiple sample bioptome of the invention is illustrated schematically in sequence. As seen in FIG. 5a, a first tissue sample is taken by positioning the jaw cups 46a, 46b around a tissue 60 to be sampled. The handle of the bioptome is operated as described above so that the cylindrical sleeve 40 is moved distally over the narrow arms 50a, 50b of the jaw assembly 44 to the position approximately shown in FIG. 5b. When the sleeve 40 is moved toward this position, the jaw cups 46a, 46b are brought close to each other and the teeth 48a, 48b of the jaw cups 46a, 46b engage the tissue 60 and bite into it. Contemporaneously, and as seen with reference to FIGS. 5f–5h, the knife sharp edge 42 of the sleeve 40 severs any tissue 60 extending from the lateral sides of the jaw cups 46a, 46b. A first sample 60a of the tissue 60 is thereby trapped between the jaw cups 46a, 46b and severed from the tissue 60. It should be noted that while taking the bite, the coil 16 is not free to stretch, as it is kept longitudinally stiff by the shrink wrap or sheath 15 which extends along the length of the coil. If desired, a wire can be used instead of the shrink wrap or sheath. The wire, which would typically be flat, would be attached to the proximal and distal ends of the coil to keep the coil in tension and prevent it from stretching as the sleeve is moved forward and a bite taken.

Figure 5D:
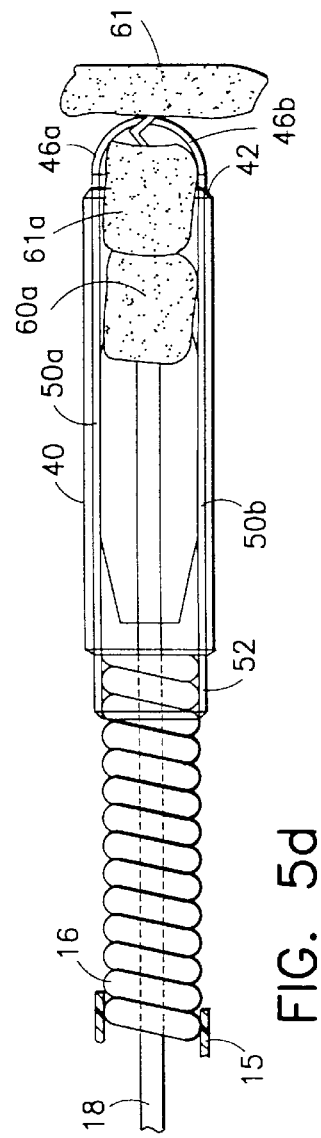
Figure 5E:
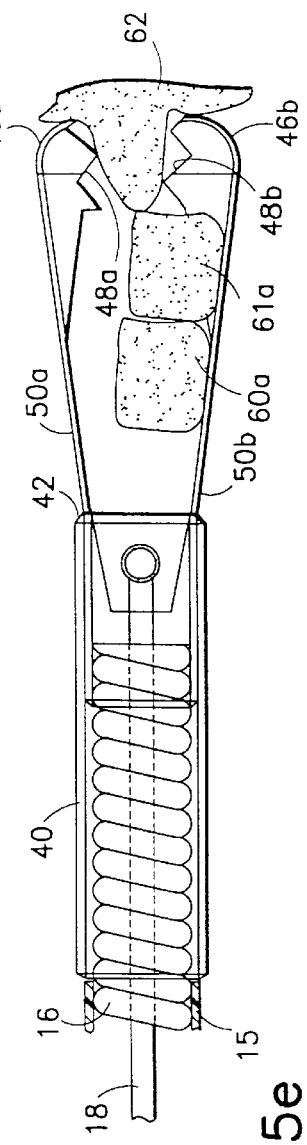

With the end effector 14 in the position approximately shown in FIG. 5b, the multiple sample bioptome may be relocated to another tissue area for sampling. The handle of the bioptome is operated as described above so that the cylindrical sleeve 40 is moved proximally over the narrow arms 50a, 50b of the jaw assembly 44 to the position approximately shown in FIG. 5c. When the sleeve 40 is moved towards this position, the jaw cups 46a, 46b are biased apart by the resilience of their respective arms 50a, 50b. The jaw cups can then be positioned around a second tissue 61 for sampling. The procedure described above with reference to FIGS. 5a and 5b is repeated. In this instance, however, as the jaw cups 46a, 46b are brought into position, the tissue 61 pushes the first sample 60a proximally away from the jaw cups 46a, 46b and into the space between the narrow arms 50a, 50b as seen in FIG. 5c. Those skilled in the art will appreciate that the tissue sample 60a is typically gummy and pliant and will stick to and move along one or both of the narrow arms 50a, 50b of the jaw assembly 44. The samples will also stick to each other. Upon the taking of a sample 61a from the tissue 61, both samples 60a and 61a are safely trapped between the narrow arms 50a, 50b of the jaw assembly 44 as shown in FIG. 5d. The procedure described above with reference to FIGS. 5a through 5d is then repeated as suggested in FIG. 5e until the space between the arms 50a, 50b is filled with samples 60a, 61a, etc. According to a presently preferred embodiment of the invention, six samples may be captured between the arms of the jaw assembly. The presently preferred dimensions of the jaw assembly are approximately 0.45 inch long by approximately 0.095 outer diameter.

FIGS. 5f–5h show a top view of the sequence of operations depicted in side views in FIGS. 5a and 5b. From the top view of FIG. 5f, it can be seen that the tissue 60 extends beyond the sides of the jaw cups 46a, 46b. The knife-sharp distal edge 42 of the cylinder 40 trims the tissue 60 which extends beyond the jaw cups to completely sever the sample 60a from the tissue 60 as shown in FIGS. 5g and 5h.

A second embodiment of the invention is shown FIGS. 6 through 8. In this embodiment, a proximal handle 112 and a distal end effector 114 are coupled by a long flexible coil 16 having an axially displaceable control wire 18 extending therethrough. The proximal handle 112 includes a central shaft 120 and a displaceable spool 122. The proximal end of the shaft 120 is provided with a thumb ring 124 and a stepped longitudinal bore 126 is provided at the distal end of the shaft 120. A longitudinal slot 128 extends from the proximal end of bore 126 to a point distal of the thumb ring 124. The displaceable spool 122 is provided with a cross member 130 which passes through the slot 128 in the central shaft 120. The cross member 130 is provided with a central hole 132 and a radially engaging set screw 134. According to this second embodiment of the invention, the proximal end of the coil 16 is fixedly mounted in the longitudinal bore 126 and the proximal end of the control wore 18 extends into the central hole 132 in the cross member 130 and is fixed there by the set screw 134. From the foregoing, those skilled in the art will appreciate that movement of the shaft 120 relative to the spool 122 results in movement of the control wire 18 relative to the coil 16. Such action results in actuation of the end effector 114 as described in detail below.

As seen in FIGS. 7 and 8, the end effector 114 according to the second embodiment of the invention includes a cylindrical sleeve 140 having a knife-sharp distal edge 142 and a jaw assembly 144. The jaw assembly 144 includes a pair of opposed jaw cups 146a, 146b each having a plurality of sharp teeth 148a, 148b. A resilient, preferably narrow arm 150a, 150b extends proximally from each jaw cup 146a, 146b. A cylindrical base member 152 joins the proximal ends of the arms 150a, 150b. As seen best in FIG. 7, the narrow resilient arms 150a, 150b are bent apart from each other urging the jaw cups 146a, 146b apart. According to the second embodiment of the invention, the proximal end of the cylindrical sleeve 140 is coupled to the distal end of the flexible coil 16 by welding, soldering, crimping, or any other suitable manner. The cylindrical base member 152 of the jaw assembly 144 is coupled to the distal end of the control wire 18 by providing the base member 152 with a lateral hole 154 which engages a bent end 18a of the control wire 18 in a manner similar to that shown in FIG. 3 in the description of the first embodiment of the invention. However, as will be described in detail herein below, other methods of coupling the control wire to the base member are possible. The base member 152 and thus the entire jaw assembly 144 is slidably mounted and axially movable within the cylindrical sleeve 140 as shown in FIGS. 7 and 8. Those skilled in the art will appreciate that this second embodiment of the invention is quite similar to the first embodiment described above except that the sleeve 140 is coupled to the coil 16 which is coupled to the central shaft 120 of the handle 112 and the jaw assembly 144 is coupled to the control wire 18 which is coupled to the spool 122. Operation of this embodiment is substantially the same as the first embodiment described above.

The jaws 44, 144 of the multiple sample bioptome of the invention may be formed in different ways. According to the presently preferred embodiment, a cylinder of 304 or 17-7 stainless spring steel preferably having a diameter just slightly smaller than the diameter of the sleeve 40, 140 is deep drawn to provide an enclosed hemispherical bottom. The bottom of the cylinder is then cut using wire electrical discharge machining (EDM) and/or laser machining. Preferably, reciprocal teeth are cut into the periphery of the cylinder bottom, thereby forming the opposed jaw cups. However, even if no teeth are formed, the opposed jaw cups are provided with sharp cutting surfaces. Continuing away from the distal jaw cups, the arms are formed by tapering up a cutout of an approximately 100–135 degree section on two sides leaving arms which each extend about 45–80 degrees around the periphery of the cylinder. The so-formed jaws are then bent away from each other to provide pre-loaded springy arms (i.e., leaf spring beams) which can be closed by the sleeve 40, 140 as described above.

Figure 9:
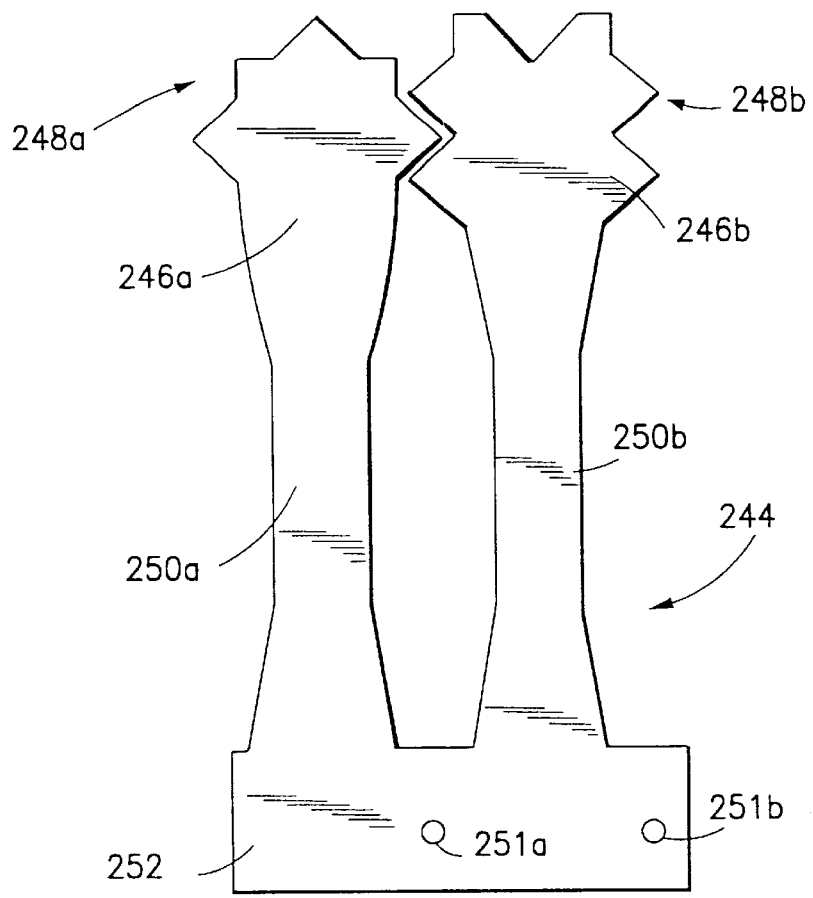
FIG. 9 is an enlarged top plan view of a sheet of punched steel which is rolled to form the jaw assembly of the invention.

According to another embodiment of the invention, the jaw assembly 44, 144 of either the first or the second embodiment may be formed from a single sheet of 0.005 inch thick 304, 17-7 steel which is cut and rolled. FIG. 9 shows a plan view of a steel sheet 244 which has been cut to form the base member 252, the narrow arms 250a, 250b, the jaw cups 246a, 246b and the jaw cup teeth 248a, 248b. Those skilled in the art will appreciate that the cutting of the sheet 244 may be accomplished in several ways, although photochemical milling (PCM) is preferred. To facilitate automation in PCM, indexing holes 251a, 251b are provided in the base member portion of the sheet 244. These holes are used to align the strip of PCM cutters in the progressive forming dies. After the sheet is cut, it is pressed and rolled to form an integral unitary jaw assembly as shown in FIGS. 2–4, 7 and 8.

As mentioned herein above, there are several ways in which the distal end 18a of the control wire 18 may be coupled to the cylindrical sleeve 40 or the base member 152 of the jaw assembly 144. While welding is the presently preferred method, FIGS. 10a through 11b show two other methods of coupling the distal end of the control wire 18 with either the sleeve or the jaw assembly.

Figures 10A, 10B:
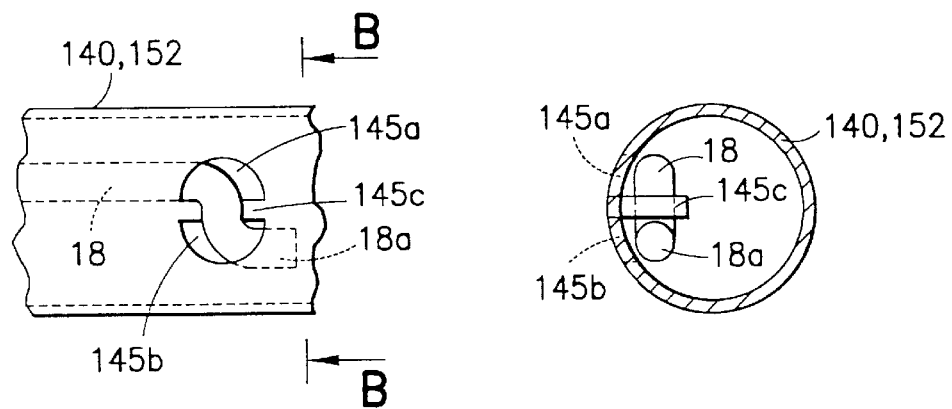

As shown in FIGS. 10a and 10b, the distal end 18a of the control wire 18 is provided with a Z-bend. The side wall of the cylindrical sleeve 40 or the base member 152 is punched with two spaced apart semicircular holes 145a, 145b leaving a bendable narrow strip 145c between them. The narrow strip 145c is bent radially inward a distance sufficient to accommodate the distal end 18a of the control wire 18. The Z-bend of the distal end 18a of the control wire 18 is inserted through the space formed between the narrow strip 145c and the semicircular holes 145a, 145b as shown in FIGS 10a and 10b.

As shown in FIGS. 11a, and 11b, the side wall of the cylindrical sleeve 40 or the base member 152 is punched with a first hole 245a and a second hole 245c which is circumscribed by the first hole 245a. The first hole 245a is preferably rectangular, semicircular, or trapezoidal in shape to form a bendable tab 245b which is bent radially inward as shown best in FIG. 11b. The Z-bend of the distal end 18a of the control wire 18 is inserted through the second hole 245c in the bendable tab 245b as shown in FIGS. 11a and 11b.

FIG. 12 shows another embodiment of a multiple sample bioptome 310 of the invention which is particularly suited for cervical biopsy procedures or other biopsy procedures where the biopsy site is approachable in a relatively short and direct path rather than through the long tortuous path of the lumen of an endoscope. In this embodiment, a proximal handle 312 is provided with a fixed portion 324 and a movable lever portion 322 which is coupled to the fixed portion by a pivot pin 323. A hollow tube 340 is coupled at its proximal end to the movable lever portion 322 of the handle 312 by a cross pin 341 or other suitable fastening means. A relatively rigid rod 318 extends through the tube 340 and is coupled at its proximal end to the fixed portion 324 of the handle 312 by means of a cross pin 319 or other suitable fastening means. The distal end of the tube 340 is provided with a knife sharp edge 342 and the distal end of the rod 318 is coupled to a jaw assembly 344 as described herein above. As shown in FIG. 12, the fixed portion 324 is provided with a lower thumb ring 324a and the movable lever portion 322 is provided with a lower finger ring 322a. The upper end 322b of the movable lever portion 322 is provided with a slot 322c for engaging the cross pin 341 and the rod 318 is provided with a slot 317 through which the cross pin passes. Those skilled in the art will appreciate that the handle 312 is manipulated using a convention hand-grip. Pivotal movement of the movable lever portion 322 of the handle 312 as indicated by the arrows 321 results in linear movement of the tube 340 as indicated by the arrows 339. It will also be appreciated that the slots 317 and 322c may be dimensioned to limit movement of the tube 340. Movement of the tube 340 relative to the rod 318 results in opening and closing of the jaw assembly 344 as described herein above. The handle 312 described above may be used with the flexible coil and pull wire described with reference to FIGS. 1 and 2 and conversely, the handle 12 described with reference to FIG. 1 may be used with the tube and rod arrangement described above with reference to FIG. 12.

It will be appreciated that all of the embodiments of the multiple sample bioptome shown in FIGS. 1–12 can be provided with a cautery capability. For example, as seen in FIG. 12, a cautery contact 398 is provided which contacts the rigid rod 318 and extends out of the fixed portion 324 of the handle 312. In addition, the tube 340 is provided with shrink wrap or other insulation 399. With the provided arrangement, when a cautery current is applied to the cautery contact 398, the jaw assembly 344 is electrified via its connection to the rod 318. Typically, cauterization would be carried out after a sample is obtained and severed from the surgical site with the jaws still located at the surgical site. Because the body of the patient acts as the second electrode (ground), current flows from the jaws into the patient at the surgical site, thereby effecting a cauterization of the surgical site rather than cauterizing the sample in the jaws.

Figure 13:
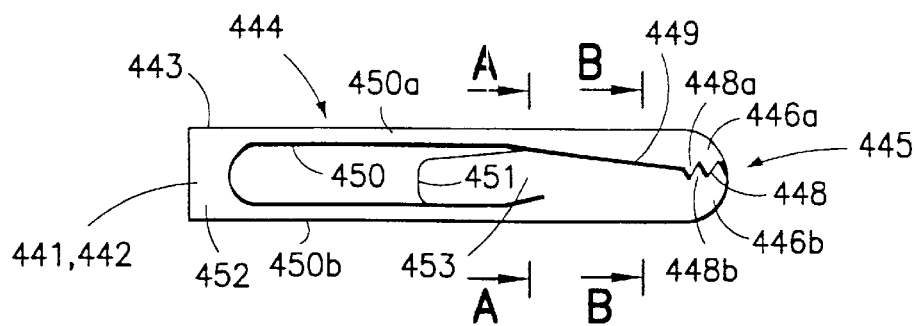
FIG. 13 is a side elevation view of a different embodiment of the jaw assembly.
Figure 13A:
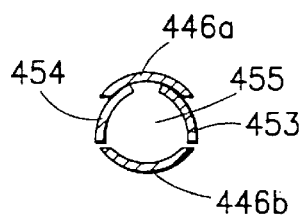
FIG. 13a is a cross sectional view along line A—A in FIG. 13.
Figure 13B:
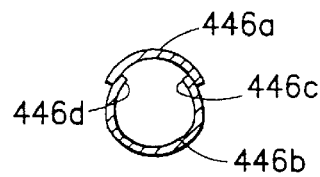
FIG. 13b is a cross sectional view along line B—B in FIG. 13.
Figure 13C:
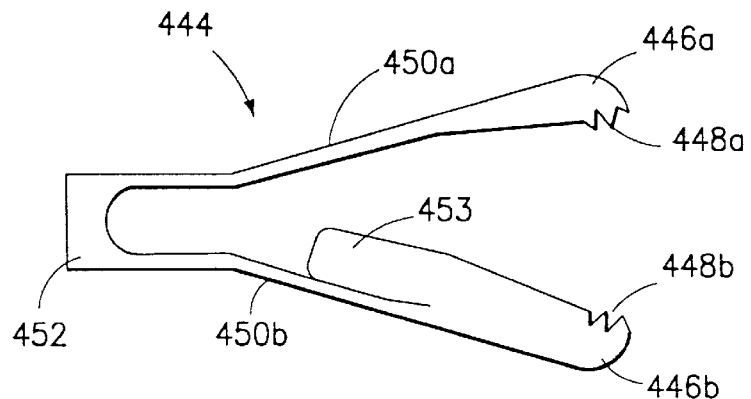
FIG. 13c is a side elevation of the jaw assembly of FIG. 13 with the jaw assembly in an open position.

FIG. 13 shows another embodiment of a jaw assembly 444. The jaw assembly 444 is preferably formed from an oblate spring steel cylinder 443 having a substantially hemispherical distal end 445 an somewhat flattened sides 441, 442. The cylinder 443 is cut using wire EDM or laser machining along a zigzag line 448 from the distal end 445 to form jaw teeth 448a, 448b and then along an upwardly inclined line 449 to form the jaw cups 446a, 446b. A substantially C-shaped cut 450 forms the arms 450a, 450b which extend from the base portion 452 to the jaw cups 446a, 446b. It is preferred that the arms 450a, 450b be as long as possible so that the jaws can be spread sufficiently far apart. In the presently preferred embodiment, the arms extend approximately 0.5–0.6 inch from the base portion to the jaw cups. The cut lines 448 and 449 are axially offset so that the lower jaw cup 446b is larger than the upper jaw cup 446a as seen best in FIG. 13b. In addition, another substantially C-shaped cut 451 is made at the proximal end of the lower jaw cup 446b to form two wings 453, 454 which are seen best in FIG. 13a. After forming the jaw assembly 444, the arms 450a, 450b are bent apart as shown in FIG. 13c. The spring steel from which the jaw assembly was formed maintains this spread apart position with resilience so that the jaws can be squeezed together to the position shown in FIG. 13 and spring apart to the position shown in FIG. 13c. According to a presently preferred embodiment, the jaw cups are bent approximately 0.25 inch apart, then closed and opened several times until the resulting opening is about 0.18 inch. The upper edges 446c, 446d of the lower jaw cup 446b are bent slightly inward as shown in FIG. 13b so that they are embraced by the upper jaw cup 446a when the jaws are closed. Similarly, the wings 453, 454 are bent radially inward as shown in FIG. 13a. The jaw assembly 444 can be used with any of the bioptome embodiments described above.

The jaw assembly 444 described above provides several important advantages. The oblate sides 441, 442 of the cylinder 443 help the teeth 448a, 448b to mesh without gaps. The long arms 450a, 450b allow for a wide opening of the jaws and for locating the spring area in the arms a sufficient distance from the distal end of the jaws so that the bending moments on the arms is low enough to avoid plastic deformation. The wings 453, 454 stabilize the jaws against rotation during opening and closing and also protect biopsy samples in several ways. The wings form a storage chamber 455 (FIG. 13a) which extends proximally from the lower jaw cup 446b and prevents accumulated biopsy samples from being squeezed laterally out from between the jaws during repeated opening and closing and protects them from being repeatedly trimmed by the sharp edge of the sliding tube. The larger lower jaw cup 446b enhances movement of biopsy samples into the storage chamber 455.

There have been described and illustrated herein several embodiments of an endoscopic multiple sample bioptome. While particular embodiments of the invention have been described, it is not intended that the invention be limited thereto, as it is intended that the invention be as broad in scope as the art will allow and that the specification be read likewise. Thus, while particular configurations of the handle have been disclosed, it will be appreciated that other types of handles could be utilized. Also, while specific couplings of the ends of the coil and control wire have been shown, it will be recognized that other types of couplings could be used with similar results obtained. Similarly, while specific couplings of the ends of the rigid tube and rod have been shown, it will be understood that other types of couplings could be used. Moreover, while particular configurations have been disclosed in reference to the jaw assembly, it will be appreciated that other configurations could be used as well. For example, while it is preferred to provide jaws with teeth, it will be appreciated that in lieu of teeth, the jaws can be provided with sharp edges which, in conjunction with the sharp cylinder, will provide a cutting ability. Furthermore, while the jaw assembly has been disclosed as being formed from a single piece of spring steel, it will be understood that different formations of the jaw assembly can achieve the same or similar function as disclosed herein. Further yet, it will be appreciated that while the apparatus of the invention was described as advantageously permitting the obtaining of multiple biopsies without removal from the surgical site, the apparatus of the invention, if desired, could still be used for obtaining single biopsies at a time. It will therefore be appreciated by those skilled in the art that yet other modifications could be made to the provided invention without deviating from its spirit and scope as so claimed.

We claim:

1. A bioptome comprising:

a proximal handle;

a distal end effector assembly including a pair of opposed jaw cups configured for obtaining a tissue sample, the end effector assembly including a resilient portion terminating in the pair of jaw cups;

a catheter portion connecting the handle to the end effector assembly, the catheter portion including an outer member and a control member extending through the outer member, the control member being axially displaceable relative to the outer member; and a cylinder coupled to a distal end of one of the outer member and the control member, wherein the end effector assembly is coupled to a distal end of the other of the outer member and the control member, wherein actuation of the handle axially displaces the cylinder relative to the end effector assembly so that the cylinder extends around the resilient portion to force the jaw cups towards each other and obtain a tissue sample.

2. The bioptome of claim 1, wherein at least a portion of the end effector assembly extends within the cylinder.

3. The bioptome of claim 1, wherein the end effector assembly includes a base member extending within the cylinder, the resilient portion extending distally from the base member.

4. The bioptome of claim 1, wherein the end effector assembly defines a space therein for storing multiple tissue samples.

5. The bioptome of claim 1, wherein each of the pair of jaw cups includes teeth.

6. The bioptome of claim 3, wherein the resilient portion includes a pair of resilient arms.

7. The bioptome of claim 1, wherein the outer member is a hollow, flexible coil and the control member is a flexible wire.

8. The bioptome of claim 1, wherein the proximal handle includes a shaft and a spool overlying the shaft and axially displaceable relative to the shaft.

9. The bioptome of claim 8, wherein a proximal end of the outer member is coupled to the spool and a proximal end of the control member is coupled to the shaft.

10. The bioptome of claim 9, wherein the distal end of the outer member is coupled to the end effector assembly and the distal end of the control member is coupled to the cylinder.

11. The bioptome of claim 8, wherein a proximal end of the outer member is coupled to the shaft and a proximal end of the control member is coupled to the spool.

12. The bioptome of claim 1, wherein the proximal handle includes a fixed handle and a movable lever pivotally coupled to said fixed handle.

13. The bioptome of claim 12, wherein a proximal end of the outer member is coupled to the movable lever and a proximal end of the control member is coupled to the fixed handle.

14. The bioptome of claim 12, further comprising a cautery contact coupled to the inner member.

15. The bioptome of claim 1, wherein the cylinder includes a sharp distal edge adapted to sever tissue extending from a side of the jaw cups.

16. A distal assembly for a bioptome having a proximal handle and a catheter portion connecting the handle to the distal assembly, the catheter portion including an outer member and a control member extending through the outer member, the control member being axially displaceable relative to the outer member, the distal assembly comprising:

a cylinder coupled to a distal end of one of the outer member and the control member; and an end effector assembly coupled to a distal end of the other of the outer member and the control member, the end effector assembly including a pair of opposed jaw cups configured for obtaining a tissue sample and a resilient portion terminating in the pair of jaw cups, wherein actuation of the handle axially displaces the cylinder relative to the end effector assembly so that the cylinder extends around the resilient portion to force the jaw cups towards each other and obtain a tissue sample.

17. The distal assembly of claim 16, wherein at least a portion of the end effector assembly extends within the cylinder.

18. The distal assembly of claim 16, wherein the end effector assembly includes a base member extending within the cylinder, the resilient portion extending distally from the base member.

19. The distal assembly of claim 16, wherein the end effector assembly defines a space therein for storing multiple tissue samples.

20. The distal assembly of claim 16, wherein each of the pair of opposed jaw cups includes teeth.

21. The distal assembly of claim 18, wherein the resilient portion includes a pair of resilient arms.

22. The distal assembly of claim 16, wherein the distal end of the outer member is coupled to the end effector assembly and the distal end of the control member is coupled to the cylinder.

23. The distal assembly of claim 16, wherein the cylinder includes a sharp distal edge adapted to sever tissue extending from a side of the jaw cups.

* * * * *